United States Patent
Won et al.

(10) Patent No.: US 10,635,885 B2
(45) Date of Patent: Apr. 28, 2020

(54) FOOT VEIN AUTHENTICATION DEVICE

(71) Applicant: LG ELECTRONICS INC., Seoul (KR)

(72) Inventors: Hyungchul Won, Seoul (KR); Hyunho Oh, Seoul (KR); Junhak Lee, Seoul (KR); Hyoungkil Yoon, Seoul (KR); Chaedeok Lee, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 16/079,503

(22) PCT Filed: Mar. 9, 2016

(86) PCT No.: PCT/KR2016/002309
§ 371 (c)(1),
(2) Date: Aug. 23, 2018

(87) PCT Pub. No.: WO2017/150754
PCT Pub. Date: Sep. 8, 2017

(65) Prior Publication Data
US 2019/0050627 A1    Feb. 14, 2019

(30) Foreign Application Priority Data

Feb. 29, 2016   (KR) .................. 10-2016-0024504

(51) Int. Cl.
*H04N 5/33*    (2006.01)
*G06K 9/00*    (2006.01)
(Continued)

(52) U.S. Cl.
CPC ........ *G06K 9/00093* (2013.01); *A61B 5/1174* (2013.01); *G01N 21/49* (2013.01);
(Continued)

(58) Field of Classification Search
CPC ........... G06K 9/00033; G06K 9/00288; G06K 9/00255; G06K 9/00087;
(Continued)

(56) References Cited

U.S. PATENT DOCUMENTS 5,131,412 A * 7/1992 Rankin ................. A61F 5/3761
128/869
5,899,863 A * 5/1999 Hatfield ................... A61B 8/06
128/916
(Continued)

FOREIGN PATENT DOCUMENTS

KR    10-2010-0033371 A    3/2010

*Primary Examiner* — Philip P. Dang
(74) *Attorney, Agent, or Firm* — Birch, Stewart, Kolasch & Birch, LLP

(57) ABSTRACT

Disclosed is a foot vein authentication device comprising: a body part having a front surface and a rear surface and on which the foot of a user is placed on the front surface; a sensor unit arranged on any one area of the body part and formed so as to detect a vein pattern on the inside of the foot of the user; and a control unit for carrying out a user authentication procedure by comparing the vein pattern received from the sensor unit, with the pre-stored vein pattern of the user, wherein the sensor unit comprises: a light source unit for emitting infrared rays at the inside of the foot of the user; and an image acquisition unit for acquiring, as an image, the vein pattern on the inside of the foot of the user, at which the infrared rays are emitted, so as to transmit the same to the control unit.

18 Claims, 5 Drawing Sheets

(51) Int. Cl.
  *G06F 21/32* (2013.01)
  *G06K 9/20* (2006.01)
  *A61B 5/1174* (2016.01)
  *G01N 21/49* (2006.01)
  *A61B 5/024* (2006.01)

(52) U.S. Cl.
  CPC .......... *G06F 21/32* (2013.01); *G06K 9/00114* (2013.01); *G06K 9/00134* (2013.01); *G06K 9/00885* (2013.01); *G06K 9/2018* (2013.01); *A61B 5/024* (2013.01); *G06K 9/00013* (2013.01); *G06K 2009/00932* (2013.01); *G06T 2207/30101* (2013.01)

(58) Field of Classification Search
  CPC .. G06K 2009/0006; G06K 2009/00932; G06F 21/32; H04N 5/33; H04N 5/2256; H04N 5/23212
  See application file for complete search history.

(56) References Cited

U.S. PATENT DOCUMENTS

| | | | | |
|---|---|---|---|---|
| 6,311,085 | B1* | 10/2001 | Meaney | A61B 5/055 600/420 |
| 6,488,377 | B2 | 12/2002 | Matsumoto | A61B 3/145 351/206 |
| 7,550,707 | B2* | 6/2009 | Hashimoto | G06K 9/20 250/221 |
| 7,944,498 | B2* | 5/2011 | Sung | G02B 7/38 348/252 |
| 8,204,476 | B2* | 6/2012 | Morimoto | G06K 9/00033 382/115 |
| 8,223,199 | B2* | 7/2012 | Kiyomizu | G06K 9/00 348/61 |
| 8,280,484 | B2* | 10/2012 | Boyden | A61B 5/02007 356/432 |
| 8,463,003 | B2* | 6/2013 | Otsubo | G06K 9/00046 382/127 |
| 8,488,050 | B2* | 7/2013 | Ueda | G03B 13/36 348/333.04 |
| 8,724,857 | B2* | 5/2014 | Derakhshani | G06K 9/00597 382/117 |
| 8,731,251 | B2* | 5/2014 | Rosqvist | G06K 9/6892 382/125 |
| 8,811,690 | B2* | 8/2014 | Dumont | G06K 9/00 382/127 |
| 8,839,720 | B2* | 9/2014 | Stewart | F41A 17/066 102/301 |
| 8,850,535 | B2* | 9/2014 | Liberman | H04L 9/3231 726/6 |
| 8,850,536 | B2* | 9/2014 | Liberman | H04L 9/0866 713/186 |
| 8,995,726 | B2* | 3/2015 | Amano | G06K 9/00885 382/115 |
| 9,089,602 | B2* | 7/2015 | Van Wyk | A61K 9/0019 |
| 9,100,825 | B2* | 8/2015 | Schultz | H04W 12/06 |
| 9,208,505 | B1* | 12/2015 | Zhou | G06Q 30/0222 |
| 9,323,912 | B2* | 4/2016 | Schultz | G06F 21/32 |
| 9,345,427 | B2* | 5/2016 | Wood | A61B 5/0059 |
| 9,408,530 | B2* | 8/2016 | Ferren | A61B 1/041 |
| 9,417,188 | B2* | 8/2016 | Ishihara | A61B 1/00009 |
| 9,553,859 | B2* | 1/2017 | Slaby | H04L 63/08 |
| 9,588,046 | B2* | 3/2017 | Ishihara | A61B 1/00009 |
| 9,654,605 | B2* | 5/2017 | Goldfain | A45C 11/182 |
| 9,672,471 | B2* | 6/2017 | Boyden | A61B 5/02007 |
| 9,772,224 | B2* | 9/2017 | Ishiguro | G01J 1/44 |
| 9,805,214 | B2* | 10/2017 | Sahu | H04W 12/0013 |
| 9,811,299 | B2* | 11/2017 | Nobutani | G06F 21/32 |
| 9,901,298 | B2* | 2/2018 | O'Connor | A61B 5/6829 |
| 9,955,900 | B2* | 5/2018 | O'Connor | A61B 5/0064 |
| 10,002,242 | B2* | 6/2018 | Jakobsson | H04L 63/0861 |
| 10,007,831 | B2* | 6/2018 | Semba | G06K 9/00087 |
| 10,019,617 | B2* | 7/2018 | Suzuki | G06F 21/32 |
| 10,019,619 | B2* | 7/2018 | Suzuki | G06F 21/32 |
| 10,028,676 | B2* | 7/2018 | Freeman | G16Z 99/00 |
| 10,121,059 | B2* | 11/2018 | Yoo | G06K 9/00228 |
| 10,201,425 | B2* | 2/2019 | Ku | A61F 2/2475 |
| 10,349,886 | B2* | 7/2019 | Sato | A61B 90/11 |
| 2007/0038118 | A1* | 2/2007 | DePue | A61B 5/1171 600/476 |
| 2007/0116330 | A1 | 5/2007 | Takiguchi | |
| 2008/0005578 | A1* | 1/2008 | Shafir | G06K 9/00067 713/186 |
| 2008/0075332 | A1 | 5/2008 | Fujisawa et al. | |
| 2008/0107309 | A1* | 5/2008 | Cerni | G06K 9/00033 382/115 |
| 2008/0317293 | A1* | 12/2008 | Sakurai | G06K 9/00013 382/115 |
| 2009/0161920 | A1* | 6/2009 | Kan | G06K 9/0004 382/115 |
| 2009/0304237 | A1* | 12/2009 | Yoshikawa | A61B 5/1172 382/116 |
| 2010/0074476 | A1* | 3/2010 | Aoki | G06K 9/00255 382/115 |
| 2010/0277314 | A1* | 11/2010 | Bradley | G07C 1/10 340/540 |
| 2011/0188711 | A1 | 8/2011 | Miura et al. | |
| 2012/0162403 | A1* | 6/2012 | Bae | H04N 7/183 348/77 |
| 2012/0194662 | A1* | 8/2012 | Zhang | G06K 9/00033 348/77 |
| 2012/0300989 | A1* | 11/2012 | Nakashima | G06K 9/00046 382/115 |
| 2015/0339696 | A1 | 11/2015 | Zhou et al. | |
| 2016/0004917 | A1* | 1/2016 | Yoshida | A61B 90/36 382/115 |
| 2017/0011210 | A1* | 1/2017 | Cheong | A61B 5/0022 |
| 2017/0206332 | A1* | 7/2017 | Piccin | G16H 50/30 |
| 2018/0014734 | A1* | 1/2018 | Rogers | A61B 5/0048 |
| 2018/0045918 | A1* | 2/2018 | Seo | G02B 9/60 |

* cited by examiner

FOOT VEIN AUTHENTICATION DEVICE

CROSS REFERENCE TO RELATED APPLICATIONS

This application is the National Phase of PCT International Application No. PCT/KR2016/002309, filed on Mar. 9, 2016, which claims priority under 35 U.S.C. 119(a) to Patent Application No. 10-2016-0024504, filed in Republic of Korea on Feb. 29, 2016, all of which are hereby expressly incorporated by reference into the present application.

TECHNICAL FIELD

The present invention relates to a foot vein authentication device using a vein pattern formed on a foot of a body.

BACKGROUND ART

Biometrics is an authentication technique that identifies individuals using specific biometric information associated with a person's body. The biometric information used for the biometric authentication includes fingerprint, voice, face, iris, palm, vein, and the like.

On the other hand, a biometric technique using vein shows high security because replication is almost impossible. The related art biometric technique using the vein is a technique for recognizing a shape of a vein of a user's back of a hand or the user's wrist, and is configured to identify the user using an image obtained by capturing the vein after irradiating infrared rays to a portion of the vein of the back of the hand or the wrist.

However, the related art biometric technique using the vein is limited only to the use of the vein of the user's back of the hand or the user's wrist, and there are some limitations in diversifying fields to which such biometric technique can be applied.

DETAILED DESCRIPTION OF THE DISCLOSURE

One aspect of the present invention is to provide a biometric authentication device capable of using a vein of another portion of a user's body other than a vein formed in the user's hand, and of more effectively identifying the vein of the corresponding portion.

In order to achieve the above aspect according to the present invention, there is provided a foot vein authentication device, including a body part having a front surface and a rear surface, wherein a user's foot is placed on the front surface, a sensor unit disposed in one area of the body part to detect a vein pattern inside the user's foot, and a controller to perform a user authentication procedure by comparing the vein pattern received from the sensor unit with a prestored user vein pattern, wherein the sensor unit includes a light source unit to irradiate infrared rays to the inside of the user's foot, and an image acquisition unit to acquire, as an image, the vein pattern of the inside of the user's foot to which the infrared rays are irradiated and transfer the acquired vein pattern image to the controller.

The sensor unit may be disposed at a lower portion of the front surface so as to be covered with the body part, and the body part may be provided with a light-transmissive layer disposed on the front surface and made of a transparent material so as to allow movement of light between the sensor unit and the user's foot.

The light-transmissive layer may be provided with an infrared filter layer to selectively transmit the infrared rays.

The light source unit and the image acquisition unit may be integrated into one body and configured to be tiltable.

A tilting angle of the light source unit and the image acquisition unit may be set to be in the range of 45 to 70° axis perpendicular to the front surface.

A light starting point at which the infrared rays are irradiated from the light source unit may be located at a position spaced apart from the light-transmissive layer by a preset distance in a direction perpendicular to the light-transmissive layer.

The light starting point may be located at a position spaced apart from the light-transmissive layer within a distance of 10 mm or less in a direction perpendicular to the light-transmissive layer.

The body part may further include a guide unit formed to correspond to a bottom surface of the user's foot to guide a position of the user's foot.

The light starting point at which the infrared rays are irradiated from the light source unit may be located at a position spaced apart from the guide unit by a preset distance in a direction parallel to the front surface.

The sensor unit may further include a light source control unit to control an amount of infrared rays irradiated from the light source unit.

The sensor unit may include first and second sensors to detect first and second vein patterns corresponding to inside of the user's both feed, respectively, and the controller may be configured to perform a user authentication procedure by comparing the first and second vein patterns received from the first and second sensors with a prestored user vein pattern.

The controller may perform the user authentication procedure using the first vein pattern received from the first sensor, and perform the user authentication procedure again by receiving the second vein pattern from the second sensor when the user authentication procedure is failed.

The device may further include an optical system disposed on an optical path of the infrared rays irradiated from the light source unit to selectively change the optical path of the infrared rays such that the infrared rays are radiated to the inside of the user's both feet. The optical system may include a rotating mirror rotatable to change the optical path by reflecting the infrared rays irradiated from the light source unit in response to the rotation, and first and second mirrors to reflect the infrared rays reflected from the rotating mirror to change the optical path of the infrared rays toward the inside of the user's both feet.

The controller may include an image enhancement unit to improve an image of the vein pattern received from the sensor unit.

The body part may further include a protrusion protruding upward from the front surface, the sensor unit may be disposed inside the protrusion to be covered with the protrusion, and the protrusion may be provided with a light-transmissive layer disposed on an outer surface thereof and made of a transparent material to allow movement of light between the sensor unit and the user's foot.

The light-transmissive layer may be provided with an infrared filter layer to selectively transmit the infrared rays.

The light source unit and the image acquisition unit may be integrated into one body and configured to be tiltable.

A tilting angle of the light source unit and the image acquisition unit may be set to be in the range of 0 to 35° with respect to an axis perpendicular to the front surface.

A light starting point at which the infrared rays are irradiated from the light source unit may be located at a position spaced apart from the front surface by a preset distance in a direction perpendicular to the front surface.

The body part may further include a guide unit formed to correspond to a bottom surface of the user's foot to guide a position of the user's foot.

The light starting point at which the infrared rays are irradiated from the light source unit may be located at a position spaced apart from the guide unit by a preset distance in a direction parallel to the front surface.

EFFECT OF THE DISCLOSURE

According to the present invention, a sensor unit may be disposed in one area of a body part where a user's foot is placed to acquire an image of a vein pattern inside the user's foot, and a controller may perform a user authentication procedure by comparing the vein pattern acquired from the sensor unit with a prestored user vein pattern. Accordingly, an application field of a biometric technique using the vein can be further expanded, thereby improving utilization of a biometric identification device.

In addition, a light source unit and an image acquisition unit constituting a sensor unit can be configured to be tiltable, and a tiltable angle of the light source unit and the image acquisition unit and a position of an optical start point where infrared rays are irradiated from the light source unit can be specified, thereby allowing more effective detection of a vein pattern of an inside of a user's foot.

BEST MODE OF THE DISCLOSURE

Figure 1A:
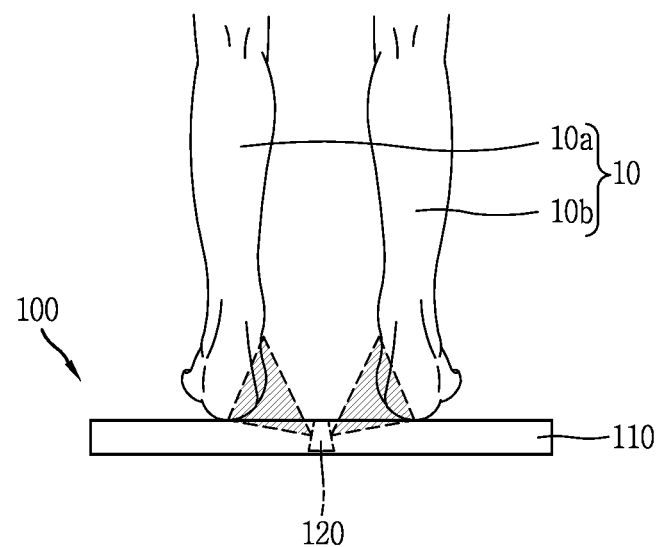
FIG. 1A is a conceptual view illustrating a state where a user's foot is placed on a foot vein authentication device according to one embodiment of the present invention.

Hereinafter, description will be given in more detail of a foot vein authentication device according to the present invention, with reference to the accompanying drawings.

A singular representation may include a plural representation unless it represents a definitely different meaning from the context.

In the different embodiments, the same or similar reference numerals are given to the same or similar components as in the previous embodiment, and a duplicate description thereof will be omitted.

In describing the present disclosure, if a detailed explanation for a related known function or construction is considered to unnecessarily divert the gist of the present disclosure, such explanation has been omitted but would be understood by those skilled in the art.

The accompanying drawings are used to help easily understand the technical idea of the present disclosure and it should be understood that the idea of the present disclosure is not limited by the accompanying drawings. The idea of the present disclosure should be construed to extend to any alterations, equivalents and substitutes besides the accompanying drawings.

Figure 1B:
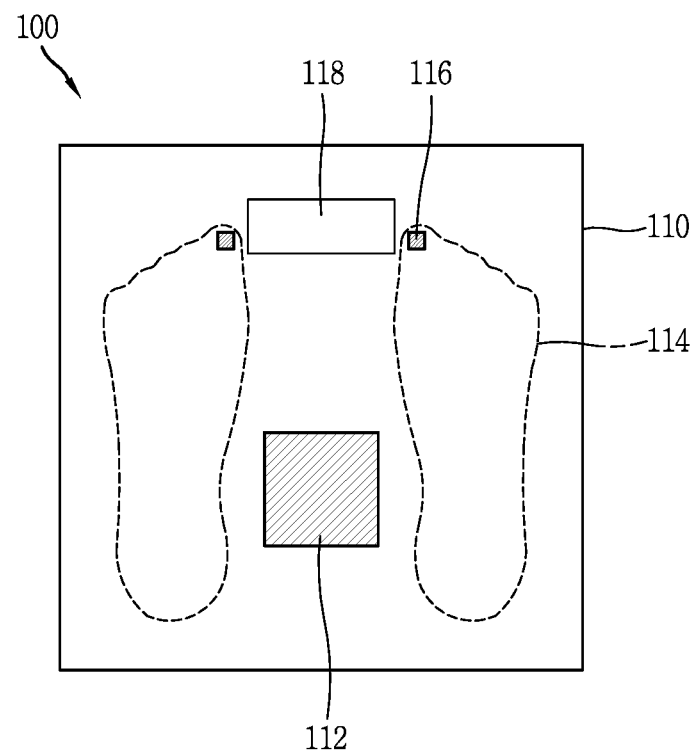
FIG. 1B is a planar view of the foot vein authentication device illustrated in FIG. 1A, viewed from a top.
Figure 1C:
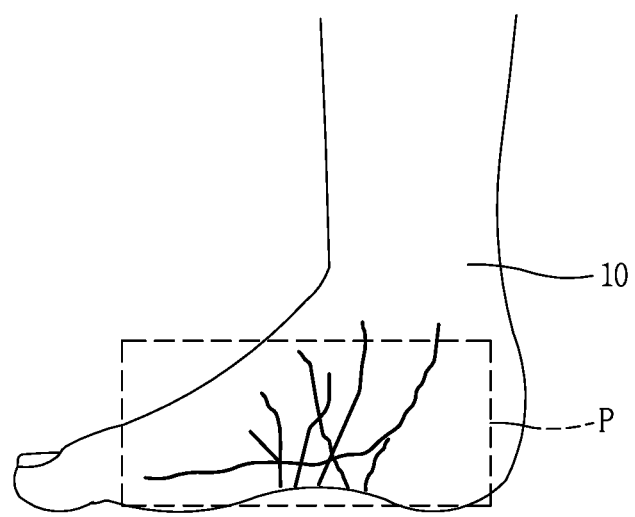
FIG. 1C is a conceptual view of a vein pattern inside a foot detected by a sensor unit illustrated in FIG. 1A.
Figure 2:
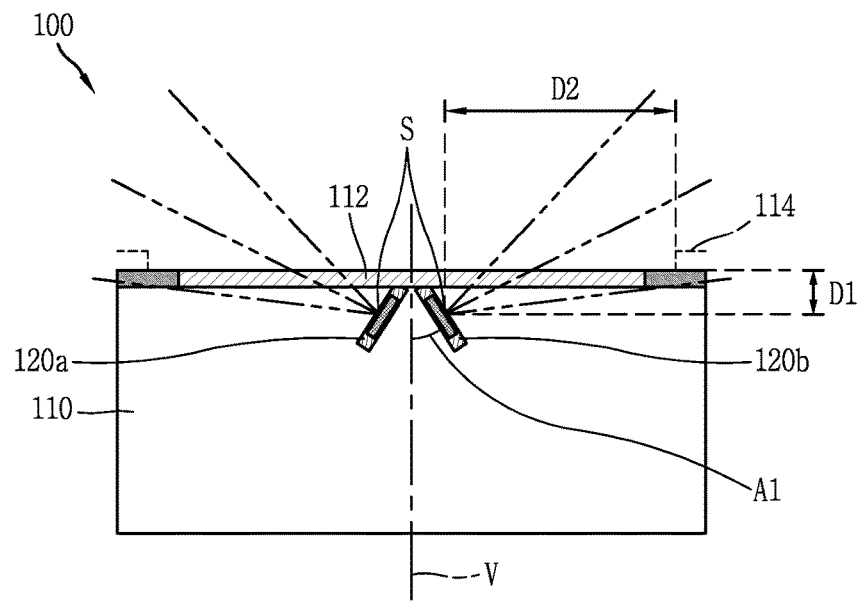
FIG. 2 is a conceptual view of an internal structure of the foot vein authentication device illustrated in FIG. 1A, viewed from a side.
Figure 3:
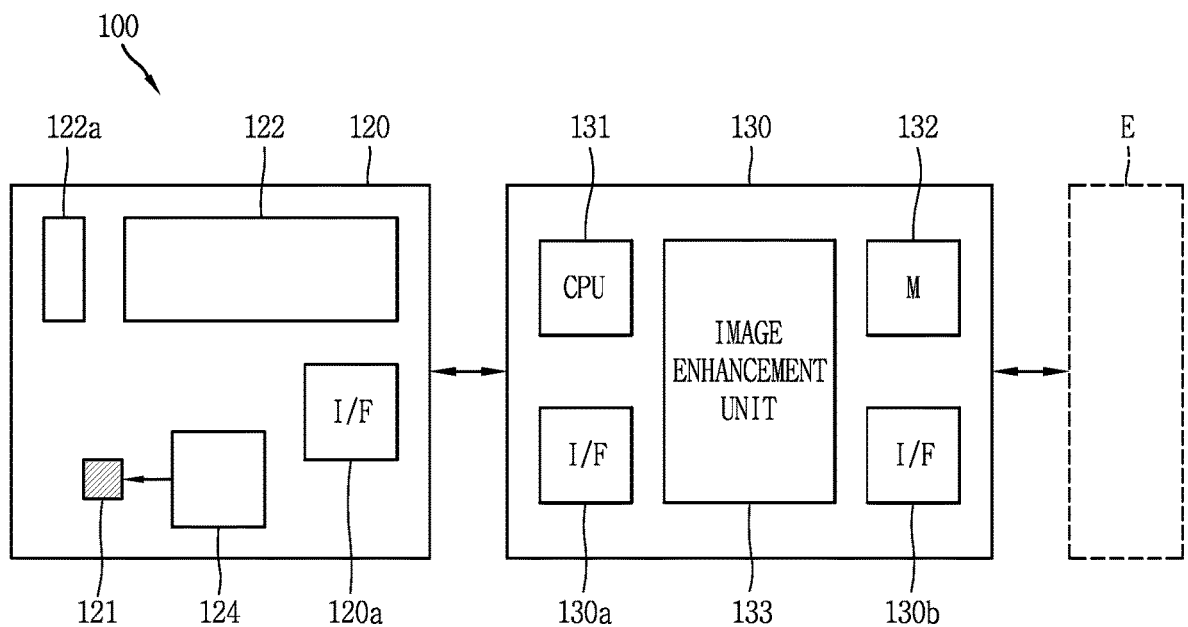
FIG. 3 is a conceptual view illustrating a configuration of the foot vein authentication device illustrated in FIG. 1A.

FIG. 1A is a conceptual view illustrating a state where a user's foot 10 is placed on a foot vein authentication device 100 according to one embodiment of the present invention. FIG. 1B is a planar view of the foot vein authentication device 100 illustrated in FIG. 1A, viewed from a top. FIG. 1C is a conceptual view of a vein pattern P inside the foot 10 detected by a sensor unit 120 illustrated in FIG. 1A. FIG. 2 is a conceptual view illustrating an internal structure of the foot vein authentication device 100 illustrated in FIG. 1A, viewed from a side. FIG. 3 is a conceptual view illustrating a configuration of the foot vein authentication device 100 illustrated in FIG. 1A.

Referring to FIGS. 1A to 3, the foot vein authentication device 100 includes a body part 110, a sensor unit 120, and a controller 130.

The body part 110 has a front surface and a rear surface, and the user's foot 10 is placed on the front surface. In addition, a left foot 10a and a right foot 10b of the user may be placed on the front surface of the body part 110, respectively. The shape of the body part 110 may be similar to a scale. Also, a display unit 118 may be disposed on the front surface of the body part 110 to output information to be provided to the user.

The sensor unit 120 is arranged in one area of the body part 110 to detect a vein pattern P inside the user's foot 10 as illustrated in FIG. 1C. The vein pattern is differently formed inside the left foot 10a and the right foot 10b of the user. The vein pattern P may thus be provided with first and second vein patterns corresponding to the inside of the left foot 10a and the inside of the right foot 10b of the user, respectively. In addition, the sensor unit 120 may include first and second sensors 120a and 120b configured to detect the first and second vein patterns, respectively.

The sensor unit 120, as illustrated in FIG. 3, includes a light source unit 121 and an image acquisition unit 122 for detecting the vein pattern P.

The light source unit 121 is configured to irradiate infrared rays to the inside of the user's foot 10, namely, to an inner area of the user's foot 10 which is exposed to outside while the user's foot 10 is placed on the front surface of the body part 110. For example, the light source unit 121 may be configured as an IR LED (not shown) for emitting (generating) infrared rays, and the IR LED may be provided in plurality.

The image acquisition unit 122 acquires the vein pattern P of the inside of the user's foot 10, to which the infrared rays are irradiated, in the form of an image and transfers the image to the controller 130. An infrared filter 122a may be disposed on a path of light incident on the image acquisition unit 122 so that the vein irradiated with the infrared rays can be fluoroscopically photographed.

The controller 130 performs a user authentication procedure by comparing the vein pattern P received from the sensor unit 120 with a prestored vein pattern P of the user. The controller 130 is provided with a central processing unit (CPU) 131 for performing calculation related to the user authentication procedure of the vein pattern P received from the sensor unit 120, and a memory 132 for storing characteristics of the received vein pattern P which is to be compared with a user vein pattern P to be registered later. The controller 130 may be connected to an external computer E so as to transfer a result of the user authentication procedure performed using the vein pattern P to the external computer E. The sensor unit 120 and the control unit 130 may be provided with interfaces 120a, 130a, and 130b which serve as paths for connecting the sensor unit 120, the controller 130, and the external computer E such that data and control signals can be transmitted and received among them.

In addition, the controller 130 may perform the user authentication procedure by comparing the first and second vein patterns received from the first and second sensors 120a and 120b with the prestored user vein pattern P.

In addition, the controller 130 may perform the user authentication procedure using the first vein pattern received from the first sensor 120a. When the user authentication process is failed due to recognition error of the vein pattern P, the controller 130 may perform the user authentication procedure again by receiving the second vein pattern from the second sensor 120b. Accordingly, it is possible to prepare for the error of the user authentication procedure or to enhance a security level of the user authentication procedure by performing the double authentication procedure with respect to the different first and second vein patterns.

In addition, the controller 130 may include an image enhancement unit 133.

The image enhancement unit 133 may enhance an image to more clearly reveal characteristics of a received vein pattern P inside the user's foot 10 detected by the sensor unit 120 before the controller 130 receives the vein pattern P and compares the received vein pattern P with the prestored user vein pattern P, thereby improving a recognition rate of the vein pattern P.

Also, the controller 130 may further include a light source control unit 124.

The light source control unit 124 is configured to control an amount of infrared rays emitted from the light source unit 121. The light source control unit 124 may be configured to control the amount of infrared rays by adjusting an exposure time of the image acquisition unit 122. Accordingly, even when brightness of a surrounding space of the foot vein authentication device 100 is changed, quality of the vein pattern P detected by the sensor unit 130 may be stably maintained at a level that enables the user authentication.

The sensor unit 120, as illustrated, may be disposed at a lower portion of the front surface of the body part 110 to be covered with the body part 110. In addition, the body part 110 may be provided with a light-transmissive layer 112.

The light-transmissive layer 112 may be disposed on the front surface of the body part 110 and may be made of a transparent material to enable a movement of light between the sensor unit 120 and the user's foot 10. The light-transmissive layer 112 may be made of, for example, glass or translucent plastic.

The light-transmissive layer 112 may include an infrared filter layer (not shown) configured to selectively transmit infrared rays. The infrared filter layer may be configured to selectively change light transmittance, and the sensor unit 120 may acquire infrared images of different ranges according to different transmittances of the infrared filter layer.

Meanwhile, the light source unit 121 and the image acquisition unit 122 may be integrated into one body and configured to be tiltable. Accordingly, as the light source unit 121 and the image acquisition unit 122 are tilted together, an infrared ray generation angle of the light source unit 121 and a capturing angle of the vein pattern P of the image acquisition unit 122 can be adjusted together.

An angle A1 at which the light source unit 121 and the image acquisition unit 122 are tilted together may be adjustable to be in the range of 45° to 70° with respect to an axis V which is perpendicular to the front surface of the body part 110. Accordingly, the recognition rate of the vein pattern P can be improved by precisely adjusting a position of the inside of the foot 10 which changes in response to the user switching it.

On the other hand, a light starting point S where infrared rays are emitted from the light source unit 121 may be set at a position spaced apart from the light-transmissive layer 112 by a preset distance D1 in a direction perpendicular to the light-transmissive layer 112. The light starting point S refers to a central portion of the infrared rays emitted from the light source unit 121.

For example, the light starting point S may be spaced apart from the light-transmissive layer 112 by a distance of 10 mm or less in the direction perpendicular to the light-transmissive layer 112. The arrangement of the light starting point S may reduce a phenomenon that the infrared rays, which are emitted from the light source unit 121 to reach the light-transmissive layer 112, are reflected at the light-transmissive layer 112 back into the body part 110 with failing to be transmitted through the light-transmissive layer 112 and proceed inside the user's foot 10, thereby allowing the infrared rays to be more accurately irradiated into the user's foot 10.

Meanwhile, the body part 110 may further include a guide unit 114.

The guide unit 114 is formed to correspond to a bottom surface of the user's foot 10 to guide the position of the user's foot 10. The guide unit 114 may be realized as a virtual image on the front surface of the body part 110 and may be varied in shape according to a size of the user's foot 10 placed on the front surface of the body part 110. The guide unit 114 may include a heartbeat sensor 116 disposed on a position corresponding to the user's toe to measure the heartbeat of the user.

The light starting point S where the infrared rays are emitted from the light source unit 121 may be located at a position spaced from the guide unit 114 by a preset distance D2 in a direction parallel to the front surface of the body part 110. For example, the light starting point S may be disposed at a position spaced apart from the guide unit 114 in the range between 35 mm to 80 mm. The light starting point S may be movable in the direction parallel to the front surface of the body part 110 so as to allow adjustment of the distance to the guide unit 114.

According to the present invention described above, first, the sensor unit 120 is disposed in one area of the body part 110 on which the user's foot 10 is placed, so as to acquire an image of the vein pattern P inside the user's foot 10, and the controller 130 compares the vein pattern P acquired through the sensor unit 120 with the prestored user vein pattern P so as to perform the user authentication procedure. Accordingly, an application field of the biometric technique using the vein can be further expanded, so as to enhance utilization of the foot vein authentication device 100.

The light source unit 121 and the image acquisition unit 122 constituting the sensor unit 120 can be tilted and the tilting angle A1 and the light starting point S where the infrared rays are emitted from the light source unit 121 are specified, and thus the vein pattern P inside the user's foot 10 can be more effectively detected.

Hereinafter, another embodiment of the foot vein authentication device 100 illustrated in FIG. 2 will be described.

Figure 4:
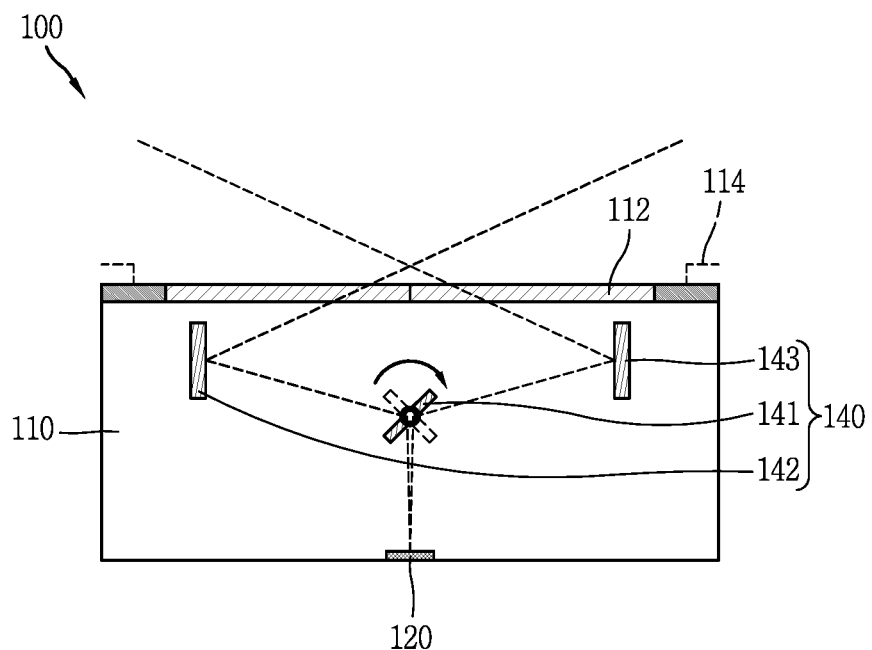
FIG. 4 is a conceptual view illustrating another embodiment of the foot vein authentication device illustrated in FIG. 2.

FIG. 4 is a conceptual view illustrating another embodiment of the foot vein authentication device 100 illustrated in FIG. 2.

Referring to FIG. 4, the foot vein authentication device 100 may further include an optical system 140.

The optical system 140 is disposed on an optical path of the infrared rays generated by the light source unit 121 (see FIG. 3), to selectively change the optical path of the infrared rays such that the infrared rays can be irradiated into the both feet 10a and 10b (see FIG. 1) of the user.

To this end, the optical system 140 may include a rotating mirror 141, a first mirror 142, and a second mirror 143.

The rotating mirror 141 is configured to be rotatable and to reflect the infrared rays emitted from the light source unit 121, in response to the rotation, thereby changing the optical path.

The first and second mirrors 142 and 143 reflect the infrared rays reflected by the rotating mirror 141, to change the optical path of the infrared rays to the inside of each of the both feet of the user, for example, the left foot 10a and the right foot 10b. According to the configuration of the optical system 140, the first and second vein patterns of the user's feet 10a and 10b can be detected using the one sensor unit 120, respectively.

Hereinafter, another embodiment of the foot vein authentication device 100 in which the sensor unit 120 is disposed in a protrusion 119 protruding upward from the body part 110 will be described.

Figure 5:
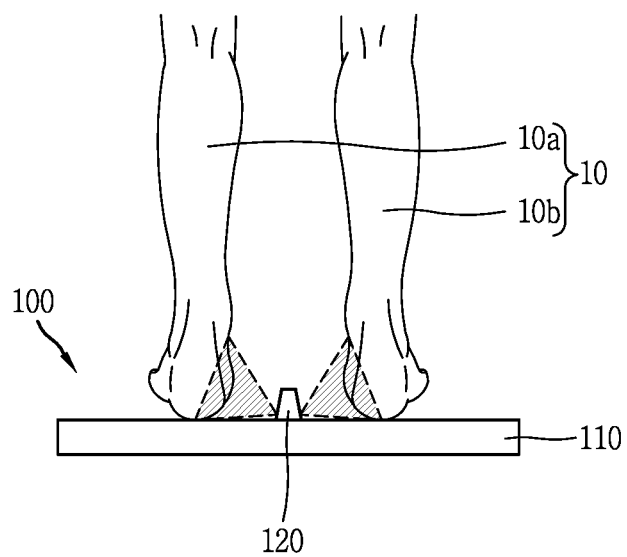
FIG. 5 is a conceptual view illustrating another embodiment of the foot vein authentication device illustrated in FIG. 1A.
Figure 6:
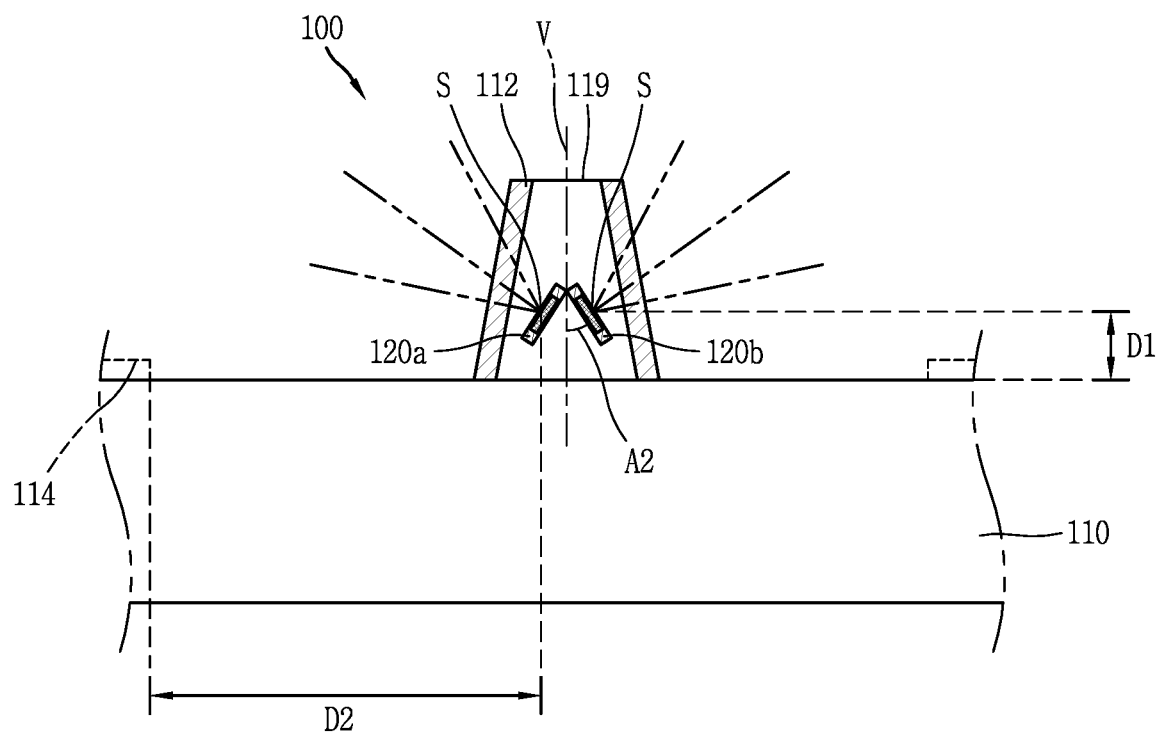
FIG. 6 is a conceptual view of an internal structure of the foot vein authentication device illustrated in FIG. 5, viewed from a side.

FIG. 5 is a conceptual view illustrating another embodiment of the foot vein authentication device 100 illustrated in FIG. 1A, and FIG. 6 is a conceptual view illustrating an internal structure of the foot vein authentication device 100 illustrated in FIG. 5.

Referring to FIGS. 5 and 6, the body part 110 may further include a protrusion 119.

The body part 110 has a front surface and a rear surface, and the user's foot 10 may be placed on the front surface.

The protrusion 119 may protrude upward from the front surface of the body part 110, as illustrated. Here, the sensor unit 120 may be arranged inside the protrusion 119 so as to be covered with the protrusion 119. The protrusion 119 may include a light-transmissive layer 112 disposed on an outer surface of the protrusion 119 and made of a transparent material so that light can move between the sensor unit 120 and the user's foot 10. In addition, the light-transmissive layer 112 may include an infrared filter layer (not shown) configured to selectively transmit the infrared rays.

Meanwhile, the light source unit 121 (see FIG. 3) and the image acquisition unit 122 (see FIG. 3) may be integrated into one body and configured to be tiltable. Here, a tilting angle A2 may be in the range between 0 to 35° with respect to an axis V which is perpendicular to the front surface of the body part 110.

On the other hand, the light starting point S at which the infrared rays are emitted from the light source unit 121 may be located at a position spaced apart from the body part 110 by a preset distance D1 in the direction perpendicular to the front surface. For example, the light starting point S may be located at a position spaced apart from the front surface of the body part 110 by a distance of 50 mm or less.

Meanwhile, the body part 110 may further include a guide unit 114.

The guide unit 114 may be formed to correspond to the bottom surface of the user's foot 10 to guide the position of the user's foot 10. The guide unit 114 may be realized as a virtual image on the front surface of the body part 110 and may be varied in shape according to a size of the user's foot 10 placed on the front surface of the body part 110.

The light starting point S at which the infrared rays are emitted from the light source unit 112 may be located at a position spaced apart from the guide unit 114 by a predetermined distance D2 in a direction parallel to the front surface of the body part 110. For example, the optical start point S may be positioned at a position spaced apart from the guide unit 114 in the range between 35 mm and 80 mm.

INDUSTRIAL APPLICABILITY

Embodiments of the present invention can be applied to various industrial fields related thereto by proposing a foot vein authentication device including a sensor unit to detect a vein pattern inside a user's foot.

The invention claimed is:

1. A foot vein authentication device, comprising:
  a body part having a front surface and a rear surface, wherein a user's foot is placed on the front surface;
  a sensor unit disposed in one area of the body part to detect a vein pattern inside the user's foot; and
  a controller to perform a user authentication procedure by comparing the vein pattern received from the sensor unit with a restored user vein pattern, wherein the sensor unit comprises:
  a light source unit to irradiate infrared rays to the inside of the user's foot; and
  an image acquisition unit to acquire, as an image, the vein pattern of the inside of the user's foot to which the infrared rays are irradiated and transfer the acquired vein pattern image to the controller,
  wherein the sensor unit is disposed in a lower portion of the front surface so as to be covered with the body part,
  wherein the body part is provided with a light-transmissive layer disposed on the front surface and made of a transparent material so as to allow movement of light between the sensor unit and the user's foot, and
  wherein the light-transmissive layer is provided with an infrared filter layer to selectively transmit the infrared rays.

2. The device of claim 1, wherein the light source unit and the image acquisition unit are integrated into one body and configured to be tiltable.

3. The device of claim 2, wherein a tilting angle of the light source unit and the image acquisition unit is set to be in a range of 45 to 700 with respect to an axis perpendicular to the front surface.

4. The device of claim 1, wherein a light starling point at which the infrared rays are irradiated from the light source unit is located at a position spaced apart from the light-transmissive layer by a preset distance in a direction perpendicular to the light-transmissive layer.

5. The device of claim 4, wherein the light starting point is located at a position spaced apart from the light-transmissive layer within a distance of 10 mm or less in a direction perpendicular to the light-transmissive layer.

6. The device of claim 1, wherein the body part further comprises a guide unit formed to correspond to a bottom surface of the user's foot to guide a position of the users foot.

7. The device of claim 6, wherein the light starting point at which the infrared rays are irradiated from the light source unit is located at a position spaced apart from the guide unit by a preset distance in a direction parallel to the front surface.

8. The device of claim 1, wherein the sensor unit further comprises a light source control unit to control an amount of infrared rays irradiated from the light source unit.

9. The device of claim 1, wherein the sensor unit comprises first and second sensors to detect first and second vein patterns corresponding to inside of the user's both feet, respectively, and wherein the controller is configured to compare the first and second vein patterns received from the first and second sensors with a restored user vein pattern so as to perform the user authentication procedure.

10. The device of claim 9, wherein the controller performs the user authentication procedure using the first vein pattern received from the first sensor, and performs the user authentication procedure again by receiving the second vein pattern from the second sensor when the user authentication procedure fails.

11. The device of claim 1, further comprising: an optical system disposed on an optical path of the infrared rays irradiated from the light source unit to selectively change the optical path of the infrared rays such that the infrared rays are radiated to the inside of the user's both feet, wherein the optical system comprises: a rotating mirror rotatable to change the optical path by reflecting the infrared rays irradiated from the light source unit in response to the rotation; and first and second mirrors to reflect the infrared rays reflected from the rotating mirror to change the optical path of the infrared rays into the user's both feet.

12. The device of claim 1, wherein the controller comprises an image enhancement unit to improve an image of the vein pattern transmitted from the sensor unit.

13. The device of claim 1, wherein the body part further comprises a protrusion protruding upward from the front surface, the sensor unit is disposed inside the protrusion to be covered with the protrusion, and the protrusion is provided with the light-transmissive layer.

14. The device of claim 13, wherein the light source unit and the image acquisition unit are integrated into one body and configured to be tiltable.

15. The device of claim 14, wherein a tilting angle of the light source unit and the image acquisition unit is set to be in a range of 0 to 350 with respect to an axis perpendicular to the front surface.

16. The device of claim 13, wherein a light starting point at which the infrared rays are irradiated from the light source unit is located at a position spaced apart from the front surface by a preset distance in a direction perpendicular to the front surface.

17. The device of claim 13, wherein the body part further comprises a guide unit formed to correspond to a bottom surface of the user's foot to guide a position of the user's foot.

18. The device of claim 16, wherein the light starting point at which the infrared rays are irradiated from the light source unit is located at a position spaced apart from the front surface by a preset distance in a direction parallel to the front surface.

* * * * *